United States Patent [19]
Costa

[11] Patent Number: 5,942,232
[45] Date of Patent: Aug. 24, 1999

[54] COMPOSITION WITH PLANT ADDITIVES AND TREATMENT METHOD FOR REDUCING STRESS LEVELS IN FISH

[75] Inventor: Anthony Costa, Montreal, Canada

[73] Assignee: Rolf C. Hagen, Inc., Montreal, Canada

[21] Appl. No.: 08/739,407

[22] Filed: Oct. 29, 1996

[51] Int. Cl.⁶ .................................................. A61K 35/78
[52] U.S. Cl. ......................................................... 424/195.1
[58] Field of Search .......................................... 424/195.1

[56] References Cited

U.S. PATENT DOCUMENTS

| | | |
|---|---|---|
| 4,500,510 | 2/1985 | Goldstein . |
| 4,596,711 | 6/1986 | Tubaro et al. . |
| 4,719,111 | 1/1988 | Wilson . |
| 4,749,503 | 6/1988 | Bennett et al. . |
| 4,853,131 | 8/1989 | Etani . |
| 4,865,773 | 9/1989 | Kim et al. . |
| 4,877,524 | 10/1989 | Eberhardt . |
| 4,882,072 | 11/1989 | Eberhardt . |
| 4,925,582 | 5/1990 | Bennett . |
| 4,980,176 | 12/1990 | Berke et al. . |
| 5,015,474 | 5/1991 | Parnell . |
| 5,082,573 | 1/1992 | Goldstein et al. . |
| 5,128,132 | 7/1992 | Parnell . |
| 5,149,534 | 9/1992 | Obayashi et al. . |
| 5,211,872 | 5/1993 | Goldstein et al. . |
| 5,273,754 | 12/1993 | Mann . |
| 5,275,943 | 1/1994 | DiTuro . |
| 5,569,459 | 10/1996 | Shlyankevich . |

OTHER PUBLICATIONS

Landysheva et al, *Kazanskii Meditsinskii Zhurnal* 58(5) 1977 pp. 84–85 Biosis Abstract only.

*Primary Examiner*—Marianne P. Allen
*Attorney, Agent, or Firm*—Wolf, Greenfield & Sacks, P.C.

[57] ABSTRACT

The invention provides a method and composition for reducing the level of stress in fish. The method involves applying an effective amount of a stress-relieving additive, such as an herbal extract, plant extract, root extract, or the like, to a solution for containing fish. Valerian root extract, chamomile flower extract, and mixtures of these can be used. An aqueous conditioner composition containing a stress-relieving additive is formulated for use with fish.

14 Claims, No Drawings

COMPOSITION WITH PLANT ADDITIVES AND TREATMENT METHOD FOR REDUCING STRESS LEVELS IN FISH

FIELD OF THE INVENTION

This invention relates generally to solutions added to fish aquariums, and more particularly to a fish aquarium conditioner composition containing an additive that reduces stress in confined fish.

DESCRIPTION OF RELATED ART

The field of aquarium conditioners involves the addition of various chemicals added to potable water to make it an environment suitable for aquatic life. When fish are confined in unnatural environments, such as in aquariums, or in plastic bags during transport, they are affected physiologically by various chemicals occurring naturally, or added to potable water supplies. Aquarium conditioners are therefore designed to eliminate, or minimize, the effects of these chemicals on the fish.

For example, a common route by which chlorine is introduced into potable water is through its use as a disinfectant. As chlorine is extremely toxic to aquatic life, a dechlorinator is an essential ingredient for an aquarium conditioner. Other typical ingredients to aquarium conditioners include chelating agents to eliminate heavy metal ions, preservatives to reduce undesired microbial activity, slime-replacing compounds to replenish the mucoprotein coating of a fishes' epidermis, and a buffering system designed to maintain a pH range for various additives designed for use in such range. All of the aforementioned additives are known to those of ordinary skill in the art of formulating aquarium conditioners, and are typically found in state-of-the-art aquarium conditioners.

The addition of Aloe Vera Gel to a fish conditioner composition, described in U.S. Pat. No. 4,500,510, issued on Feb. 19, 1985 and incorporated herein by reference, was intended to improve the slime-coat replacement ability of an aquarium conditioner containing slime-coat replacing agents. The aquarium conditioner described therein includes the addition of aloe vera extract to promote healing of damaged fish tissue caused by, for example, scraping, bites from other fish or animals, netting, handling, wounds, ammonia burns, or as the result of bacterial, fungal or parasitic infection. The "treatment" consists of topically administering the aloe vera gel to fish by adding it to, for example, an aquarium containing fish having damaged tissue. The aloe vera gel acts to more quickly complete the slime-coat replacement of the damaged fish tissue. A fishes' slime-coat acts as a shield against irritants, disease causing organisms, and as barrier to prevent the loss of internal electrolytes and body fluids.

Environmental stress on fish occurs during handling, transportation, netting, or confinement in aquariums. Stress in fish is also especially evident when they are placed in a small volume of water, which leaves them much less room in which to swim around, and which subjects them to increased concentrations of harmful by-products and toxic chemicals.

Plant extracts are used on humans for their purported therapeutic and medicinal properties. For example, tea with chamomile is promoted as a relaxant. In addition to its use as a relaxant, chamomile is known to contain azulene and alpha bisabolol, which are known for their anti-inflammatory properties. Valerian, as well as other plant extracts, is included in an over the counter mild sedative under the name Relaxen, manufactured by Natural Health Ltd. The use of valerian root extract and chamomile flower extract are known to produce calming effects in humans, but no prior art fish aquarium conditioners are known to use them for treating non-mammals. What is needed in the art is a method of treatment to reduce stress in fish, and a composition that is effective for such use when added directly to water containing fish, or when incorporated into a composition added to water containing fish.

SUMMARY OF THE INVENTION

The present invention is directed to methods and compositions for treating fish to reduce stress. The invention is based on the discovery that herbal extracts, plant extracts root extracts, and mixtures thereof affect the nervous system of fish to reduce their stress level.

A composition having features of the present invention is an aqueous conditioner composition formulated for use with fish which includes at least one stress-relieving additive in an amount effective for relieving stress in a fish. In one embodiment of the invention the stress-relieving additive is a non-aloe vera extract and may be selected from the group consisting of herbal extracts, plant extracts, root extracts and mixtures thereof. Preferably the stress-relieving additive is selected from the group consisting of valerian root extract, chamomile flower extract and mixtures thereof.

Optionally the aqueous conditioner composition includes a supplemental conditioner composition containing known fish conditioner additives such as a slime-replacing compound, a dechlorinator, an anti-microbial preservative, a heavy metal chelating agent, and a buffering system. In a preferred embodiment the at least one additive is present in an amount of from about 0.10 to about 0.30 weight percent; the at least one slime-replacing compound is present in an amount of about 1.3 weight percent; the dechlorinator is present in an amount of about 2.0 weight percent; the preservative is present in an amount of about 0.20 weight percent; the chelating agent is present in an amount of about 0.74 weight percent; and the buffering system is present in an amount of about 1.125 weight percent. In yet another preferred embodiment of the invention the at least one slime-replacing compound is selected from the group consisting of polyvinylpyrrolidone and carboxymethyl cellulose and mixtures thereof; the dechlorinating agent is selected from the group consisting of sodium thiosulfate, sodium metabisulfate, sodium sulfite and other oxygen containing sodium compounds; the preservative is a sodium hydroxymethylglycinate solution; the chelating agent is ethyienediaminetetraacetic acid; and the buffering system is sodium citrate and citric acid, wherein the sodium citrate is present in an amount of about 0.975 percent by weight, based on the total weight of the composition, and the citric acid is present in an amount of about 0.15 percent by weight, based on the total weight of the composition. In one embodiment the pH of the composition is between 4 and 10, and the sodium citrate chelates copper and iron. In another embodiment, the pH of the composition is greater than 6.0, and the chelating agent chelates alkaline metals. Preferably, the at least one slime-replacing compound includes a mixture of polyvinylpyrrolidone and carboxymethyl cellulose, wherein the polyvinylpyrrolidone is present in an amount of about 1.30 weight percent, based on the total weight of the composition, and wherein the carboxymethyl cellulose is present in an amount of about 0.3 weight percent, based on the total weight of the composition.

Optionally, the aqueous conditioner composition has a viscosity of 20 centipoise measured with a Brookfield viscometer at 25° C. In one embodiment the aqueous conditioner composition has a specific gravity of 1.025 measured at 16.8° C. In another embodiment the aqueous conditioner composition has a specific gravity of 1.03 measured at 25° C.

According to another aspect of the invention, an improved aquarium conditioner is provided. The aquarium conditioner is an aqueous system, wherein the improvement is a buffer system including at least one conjugate acid/base pair formulated to provide the system with a pH of about 7.8 to about 9.8. The buffer includes a chelating agent able to chelate bivalent and trivalent heavy metal ions in an aqueous solution. In one embodiment the conjugate acid/base pair is sodium citrate and citric acid.

According to another aspect of the invention, methods of treating fish for stress are provided. A method for treating fish involves the step of administering to a fish at least one stress-relieving additive in an amount effective to promote stress reduction in the fish. The stress-relieving additive may be any of the stress-relieving additives useful in the composition of the invention and may be administered internally or topically. The stress-relieving additive can be included in an aqueous conditioner composition, optionally containing a supplemental conditioner composition, which is added directly to water containing the fish, or the additive itself can be added directly to the water containing the fish. When the additive is added directly to the water itself, an aqueous conditioner composition containing a supplemental conditioner composition may optionally be added directly to the water in an additional step. The aqueous conditioner composition and the supplemental conditioner composition may be any of the aqueous conditioner compositions and supplemental conditioner compositions useful in the compositions of the invention described above.

These and other features, aspects and advantages of the present invention will become better understood with reference to the following description and appended claims.

DETAILED DESCRIPTION OF THE PREFERRED EMBODIMENT

The present invention relates to a composition including at least one stress-relieving compound, to an aquarium conditioner including at least one stress-relieving compound and to a method of treatment for stress in fish that involves delivering at least one stress-relieving compound to fish in water in an amount effective to reduce stress in fish.

A composition of the present invention includes at least one stress-relieving additive. As used herein, a "stress-relieving additive" is a compound that, when added to water containing fish, produces a reduction in the visible manifestations of stress in fish. Preferably the stress-relieving additive is a non-aloe vera extract selected from the group of herbal extracts, plant extracts, root extracts, and mixtures thereof. In a preferred embodiment, the stress-relieving additive is a valerian root extract, a chamomile flower extract, or a mixture thereof. A mixture of a solid extract of valerian root and a liquid extract of chamomile flowers is particularly effective in reducing the visible manifestations of stress in fish.

The level of stress in a fish may be determined by analyzing a variety of parameters, such as an individual assessment of the interactions between fish sharing a common aquarium, the rate and type of movement of individual fish, and the physiological healing of irritated or damaged tissue resulting from trauma or environmental stresses such as that caused by netting, and transferring of aquarium fish from one tank to another. One of ordinary skill in the art may determine if a particular compound is a stress-relieving additive and therefore functions to reduce the visible manifestations of stress in fish by observing the behavior of the fish and the physiological condition of the fish. Fish which have reduced levels of stress show less nervous excitability, that is, they exhibit fewer incidences of biting one another, rapid darting movements, and hitting the walls of the container.

The term "fish" as used herein includes all aquatic animal life such as turtles, salt water fish, fresh water fish, etc.

The composition of the invention is an aqueous conditioner composition which is formulated for use with fish. A composition which is "formulated for use with fish" encompasses those compositions which have a suitable salt concentration, pH, etc., for maintaining aquatic life and additionally, those compositions which although unsuitable for use with aquatic life in their stored forms, include directions for mixture, such as dilution, that would render the composition suitable for aquatic life. The conditions which are suitable for aquatic life are well known to those of ordinary skill in the art.

The term "aqueous conditioner composition", as used herein, is meant to define a composition suitable for use in an aquarium that when added to a container of water, will reduce or eliminate the toxic effects on fish of by-products or chemicals added to water. A preferred aqueous conditioner composition includes a supplemental conditioner composition having at least one slime-replacing compound to promote fish slime coat replacement, a dechlorinator to neutralize chlorine in water, a preservative to reduce microbial activity to a safe level for fish, a chelating agent to eliminate the toxic effects of heavy metals on fish, and a buffering system to stabilize the pH of the composition.

The stress-relieving additives are added to the aqueous conditioner composition of the present invention in an amount that is effective to relieve stress in fish, after dilution by an appropriate amount of water. Preferably, the total amount of stress-relieving additive present in the composition is about 0.10 to about 0.30 percent, by weight, of the total composition. The most preferred embodiment includes about 0.10 percent, by weight, of the total composition, of solid valerian root extract, and about 0.20 percent, by weight, of the total composition, of fluid extract of chamomile flowers.

The aqueous conditioner of the present invention preferably includes a buffering system to maintain the pH of the water at a level which is safe for fish, but at the same time to maintain the pH of the water at a level which will allow the components of the supplemental conditioner composition as well as the stress-relieving additive to function properly. The preferred buffering system is citric acid/sodium citrate, although other conjugate acid-base pairs may be suitable. The citric acid/sodium citrate buffer system is preferred because it is highly effective and inexpensive. In addition to buffering the aqueous conditioner, the citric acid component also chelates some bivalent and trivalent heavy metal ions such as copper and iron.

The aqueous conditioner composition preferably also contains at least one slime-replacing compound. A "slime-replacing compound" as used herein is a compound which aids in the replacement of the fish slime coat. Such compounds are readily available commercially and include, for example, polyvinylpyrrolidone, carboxymethyl cellulose, etc. BASF manufactures polyvinylpyrrolidone under the trade name PVP K-30, which is an extremely effective slime-replacing compound. Polyvinylpyrrolidone is not metabolized and under normal use does not modify physiological functions in living things. Thus, polyvinylpyrrolidone is almost biologically inert. In addition, polyvinylpyrrolidone is neither a sensitizer nor an irritant, is non-toxic, and stable at temperatures between 78–84° F. Another effective and commonly used slime-coat replacement compound is carboxymethyl cellulose, available commercially by the name WaloCel-CRT10,000 GA. The preferred embodiment of the present invention includes both polyvinylpyrrolidone in an amount of about 1.30 percent, by weight, of the composition, and carboxymethyl cellulose in an amount of about 0.30 percent, by weight, of the composition.

The aqueous conditioner composition of the present invention preferably also includes a "dechlorinator". A "dechlorinator" according to the invention is a composition which neutralizes free, combined, and residual chlorine in water. Sodium thiosulfate, sodium metabisulfate, sodium sulfite, the thiosulfate families of compounds, as well as other oxygen-containing sodium compounds are extremely effective dechlorinating agents, although other compounds may be suitable. The preferred embodiment includes anhydrous sodium thiosulfate in an amount of about 2.0 percent, by weight, of the composition, which effectively dechlorinates water.

Preferably, anti-microbial preservatives also are added to the aqueous conditioner of the present invention. In a preferred embodiment the anti-microbial preservation is Suttocide A, which is a 50% aqueous solution of sodium hydroxymethylglycinate, and is very effective as a broad spectrum anti-microbial agent, and against yeast and molds. Suttocide A remains active in the pH range of the aqueous conditioner of the present invention, exhibits very low toxicity towards aquatic life at recommended use levels, and has no known incompatibilities. The amount of Suttocide A included in the aqueous conditioner of the present invention is preferably about 0.20%.

Additionally, a heavy metal chelating agent is a preferred component of the aqueous conditioner composition of the present invention. A heavy metal chelating agent is one which interacts with divalent and trivalent heavy metal ions. An extremely effective compound for this use is ethylenediaminetetraacetic acid (hereinafter "EDTA"). The amount of EDTA included in the preferred embodiment is about 0.74 percent, by weight, of the composition. The preferred embodiment includes a commercially available 37% aqueous solution of the tetra sodium salt of EDTA, by the name of Versene 100. Versene 100 is recommended for use at pH levels greater than 6.0.

In one embodiment of the invention, the pH of the composition is between 4 and 10, such that the sodium citrate chelates copper and iron. In another embodiment, the pH of the composition is greater than 6.0, such that the chelating agent chelates alkaline metals.

In another embodiment of the invention, the composition has a viscosity of 20 centipoise as measured by a Brookfield viscometer at 25° C. In a preferred embodiment, the composition has a specific gravity of 1.025 measured at 16.8° C. In another preferred embodiment, the composition has a specific gravity of 1.03 measured at 25° C.

The method of the invention is a method of treating a fish for stress. The method involves the step of adding the above-described compositions to water containing the fish in order to produce a concentration of stress-relieving additive in the water which is effective to promote stress reduction in the fish. The concentration of stress-relieving additive which is effective to reduce stress in fish is discussed above in more detail. Generally, small concentrations of the aqueous conditioner composition, including the stress-relieving additive, are necessary to reduce the level of stress in fish. For example, adding approximately 5 ml of the aqueous conditioner composition containing the supplemental conditioner composition of the present invention to 35–40 liters of water is effective to both condition the water, and to produce a reduction in the level of stress in fish in the water. The stress-relieving additive may be administered topically or internally to the fish by being added directly to the water in which the fish is contained.

In one embodiment of the invention, the stress-relieving additive may be added directly to the water without being first mixed with an aqueous conditioner composition. In another embodiment, the stress-relieving additive may be added to an aqueous conditioner composition and then the mixture of the aqueous conditioner composition and the stress-relieving additive may be added to the water. The compositions may be added to the water of any vessel in which the fish are contained. For example, the compositions may be added to the water of a temporary vessel used for transportation of the fish, such as a plastic bag, containing water. The compositions useful in the methods of the invention are a stress-relieving additive composition alone as well as any of those compositions described above in relation to the composition claims.

Example #1

Preparation of Fish Aquarium Conditioner Composition with Valerian and Chamomile Part A: Into a suitably clean and sanitized stainless steel tank equipped with a variable speed mixer, 60% of the total required water is added. With the mixer turned on at high speed the PVP K-30 is added slowly to the vortexing water. Once the PVP K-30 is completely dissolved, Walocel-CRT10,000 GA powder is gradually added to the mixture in order to avoid lump formation. The solution is mixed until a clear homogeneous mixture is obtained.

Part B: To a second suitably clean and sanitized stainless steel tank equipped with a mixing device, 20% of the required water is added. With the mixer on high speed, the Versene 100 is added, followed by the sodium citrate, and the citric acid. The aqueous solution is mixed until it becomes clear. If required, additional citric acid may be added to achieve a pH of 9.2.

Part C: To a third suitably clean and sanitized stainless steel tank equipped with a mixing device, 20% of the required water is added. With the mixer on high speed, the sodium thiosulfate anhydrous, Suttocide A, solid valerian root extract and chamomile extracts are successively added. The aqueous solution is mixed until all are dissolved.

With the mixing device on slow speed, add part B to part A until completely blended. With the mixing device on slow speed, add part C to the mixture of A and B. With the mixing device on slow speed, continue to mix for 15 minutes until fully blended.

Example #2

Controlled Test Of Aquarium Conditioner On Fish

Two separate clean containers were labeled "A" and "B", and filled with tap water. Enough fish were then added to both containers to produce very crowded conditions, causing them to exhibit visible symptoms of stress, including biting each other, extremely rapid darting movements, and frequently swimming into the container walls. Into container "A" was added an amount of the aquarium conditioner composition of the present invention effective to condition the tap water to make it suitable for aquatic life and to reduce visible stress levels in fish. Into container "B" was added an amount of a comparable aquarium conditioner composition, without valerian root and chamomile flower extracts, effective to condition the water for fish.

The fish in each container were observed over a period of several hours. Fish in container "A" stopped biting each other, moved more slowly, and hit the container walls less frequently. In addition, the fish in container "A" tended to hover in the lower regions of the container. Fish in container "B" continued to bite each other, to exhibit rapid darting movements, and to hit the container walls.

What is claimed is:

1. An aquarium conditioner including an aqueous composition comprising:
    at least one stress-relieving additive in an amount effective for relieving the visible manifestations of stress in a fish,
    wherein the at least one stress relieving additive comprises a mixture of valerian root extract and chamomile flower extract.

2. The aqueous composition of claim 1, further comprising a supplemental composition the supplemental composition comprising:
    at least one slime-replacing compound;
    a dechlorinator;
    an antimicrobial preservative;
    a chelating agent; and
    a buffering system that maintains the pH of the composition from about 7.8 to about 9.8.

3. The aqueous composition of claims 2, wherein the mixture of valerian root extract and chamomile flower extract is present in an amount of from about 0.10 to about 0.30 weight percent, based on the total weight of the composition;
    the at least one slime-replacing compound is present in an amount of about 1.3 weight percent, based on the total weight of the composition;
    the dechlorinator is present in an amount of about 2.0 weight percent, based on the total weight of the composition;
    the preservative is present in an amount of about 0.20 weight percent, based on the total weight of the composition;
    the chelating agent is present in an amount of about 0.74 weight percent, based on the total weight of the composition; and
    the buffering system is present in an amount of about 1.125 weight percent, based on the total weight of the composition.

4. The aqueous composition of claim 2, wherein
    the at least one slime-replacing compound is selected from the group consisting of polyvinylpyrrolidone and carboxymethyl cellulose and mixtures thereof;
    the dechlorinating agent is selected from the group consisting of sodium thiosulfate, sodium metabisulfate, sodium sulfite and other oxygen containing sodium compounds;
    the preservative comprises a sodium hydroxymethylglycinate solution;
    the chelating agent comprises ethylenediaminetetraacetic acid; and
    the buffering system comprises sodium citrate and citric acid.

5. The aqueous composition of claim 4, wherein the at least one slime-replacing compound comprises a mixture of polyvinylpyrrolidone and carboxymethyl cellulose.

6. The aqueous composition of claim 5, wherein
    the polyvinylpyrrolidone is present in an amount of about 1.30 weight percent, based on the total weight of the composition; and
    the carboxymethyl cellulose is present in an amount of about 0.3 weight percent, based on the total weight of the composition.

7. The aqueous composition of claim 4, wherein
    the sodium citrate is present in an amount of about 0.975 percent by weight, based on the total weight of the composition; and
    the citric acid is present in an amount of about 0.15 percent by weight, based on the total weight of the composition.

8. The aqueous composition of claim 7, wherein the sodium citrate chelates copper and iron in a composition having a pH of between 4 and 10.

9. The aqueous composition of claims 4, wherein the chelating agent chelates alkaline metals in a composition having a pH of greater than 6.0.

10. The aqueous composition of claim 1, wherein the composition has a viscosity of 20 centipoise measured with a Brookfield viscometer at 25° C.

11. The aqueous composition of claim 10, wherein the composition has a specific gravity of 1.025 measured at 16.8° C.

12. The aqueous composition of claim 13, wherein the composition has a specific gravity of 1.03 measured at 25° C.

13. The aqueous composition of claim 1, wherein the the valerian root extract is solid and the chamomile flower extract is liquid.

14. A The aqueous composition of claim 13, wherein the concentration of the solid valerian root extract is about 0.10 percent, by weight, of the total composition, and the concentration of the liquid chamomile flower extract is about 0.30 percent, by weight, of the total composition.

* * * * *